US010532403B2

(12) United States Patent
Tessier et al.

(10) Patent No.: US 10,532,403 B2
(45) Date of Patent: Jan. 14, 2020

(54) SIZE-TUNABLE NANOPARTICLE SYNTHESIS (71) Applicant: UNIVERSITEIT GENT, Ghent (BE)

(72) Inventors: Mickael Tessier, Zwijnaarde (BE); Dorian Dupont, Ghent (BE); Zeger Hens, Ghent (BE)

(73) Assignee: UNIVERSITEIT GENT, Ghent (BE)

( * ) Notice: Subject to any disclaimer, the term of this patent is extended or adjusted under 35 U.S.C. 154(b) by 325 days.

(21) Appl. No.: 15/559,534

(22) PCT Filed: Mar. 17, 2016

(86) PCT No.: PCT/EP2016/055750
§ 371 (c)(1),
(2) Date: Sep. 19, 2017

(87) PCT Pub. No.: WO2016/146719
PCT Pub. Date: Sep. 22, 2016

(65) Prior Publication Data
US 2018/0093324 A1 Apr. 5, 2018

(30) Foreign Application Priority Data

Mar. 19, 2015 (EP) .................... 15159856

(51) Int. Cl.
B22F 1/00 (2006.01)
B01J 13/00 (2006.01)
B82Y 40/00 (2011.01)
C07F 9/22 (2006.01)
C09K 11/02 (2006.01)
(Continued)

(52) U.S. Cl.
CPC .............. B22F 1/0018 (2013.01); B01J 13/00 (2013.01); B22F 1/0085 (2013.01); B82Y 40/00 (2013.01); C07F 9/224 (2013.01); C09K 11/02 (2013.01); C09K 11/07 (2013.01); C09K 11/0827 (2013.01); C09K 11/626 (2013.01); B22F 2203/11 (2013.01); B22F 2301/30 (2013.01);
(Continued)

(58) Field of Classification Search
CPC .............................. B22F 1/0018; B82Y 40/00
USPC ........................................................ 75/371
See application file for complete search history.

(56) References Cited

U.S. PATENT DOCUMENTS

2009/0315446 A1 12/2009 Murase et al.
2014/0084212 A1 3/2014 Kikuchi

FOREIGN PATENT DOCUMENTS

EP 2599898 A1 6/2013
JP 2014015549 A 1/2014

OTHER PUBLICATIONS

Extended European Search Report from EP Application No. 15159856. 2, dated Aug. 28, 2015.
(Continued)

Primary Examiner — Weiping Zhu
(74) Attorney, Agent, or Firm — Workman Nydegger (57) ABSTRACT A method for synthesizing nanoparticles with a predetermined size at high or full yield comprises mixing a first precursor material comprising a first compound comprising a halide moiety and a metal or a metalloid, a second precursor material comprising a second compound comprising a polyatomic nonmetal, and a solvent. The method further comprises heating the mixture to colloidally form nanoparticles comprising the polyatomic nonmetal and the metal or metalloid. The halide moiety is selected such as to colloidally form the nanoparticles in a predetermined size range that is at least partially determined by this halide moiety.

15 Claims, 5 Drawing Sheets

(51) Int. Cl.
*C09K 11/07* (2006.01)
*C09K 11/08* (2006.01)
*C09K 11/62* (2006.01)

(52) U.S. Cl.
CPC ..... *B22F 2998/10* (2013.01); *C09K 2211/188* (2013.01)

(56) References Cited

OTHER PUBLICATIONS

International Search Report and Written Opinion from PCT Application No. PCT/EP2016/055750, dated May 18, 2016.
Database WPI, Thomas Scientific, London, Great Britain, Jan. 30, 2014, 2 pages.
Song, et al., "Amine-derived Synthetic Approach to Color-tunable InP/ZnS Quantum Dots with High Fluorescent Qualities", Journal of Nanoparticle Research, vol. 15, No. 6, Jun. 7, 2013, 10 pages.

SIZE-TUNABLE NANOPARTICLE SYNTHESIS

FIELD OF THE INVENTION

The invention relates to the field of colloidal synthesis of nanocrystals. More specifically it relates to a method for synthesizing nanocrystals.

BACKGROUND OF THE INVENTION

Colloidally synthesized nanocrystals, e.g. semiconductor nanocrystals, such as quantum dots (QD) are a class of materials that offer various promising applications in fields related to light emission and absorption, e.g. in fields such as in-vivo imaging, light-emitting device manufacture, photodetection and solar energy conversion. For example, quantum dots may find application in transistors, solar cells, LEDs, diode lasers, medical imaging, quantum computing and a variety of other fields. Furthermore, QDs emitting in the visible electromagnetic spectrum may be of particular interest for lighting and display applications, e.g. for high brightness LEDs. A quantum dot may be sufficiently small to exhibit distinct quantum mechanical properties. A single QD can for example contain about 100 to even 100000 atoms, having a diameter that ranges from about 10 to 50 or more atoms, e.g. a diameter in the range of about 2 to about 10 nanometers. For example, three-dimensional confinement of the nanocrystal exciton states can be achieved, such that intermediate properties are obtained between those of the bulk material and discrete molecules. Therefore, the characteristics of a quantum dot may be closely related to its size and shape, e.g. the band gap, which determines the frequency range of emitted light, may be inversely related to its size.

Monodisperse ensembles of QDs may feature a narrow, size-tunable emission spectrum in combination with a broad absorption and excitation spectrum, while also being particularly suitable for solution-based processing. Colloidal synthesis of nanocrystals may comprise the synthesis from precursor compounds in a solution. When heating the solution, the decomposed precursors form monomers that nucleate. Known QDs obtainable by colloidal synthesis may comprise binary compounds, such as lead sulfide, lead selenide, cadmium selenide, cadmium sulfide, indium arsenide and indium phosphide, or ternary compounds such as cadmium selenide sulfide. Particular nanocrystals known in the art may involve cadmium chalcogenide based materials where especially CdSe QDs synthesis is a fully mastered process. Such nanocrystal can be easily manufactured due to the simplicity of their synthesis, and may have a high optical quality. However, cadmium is a toxic heavy element which may be subject to legal restrictions, e.g. by the EU ROHS directive. Consequently, the use of such materials in large amounts is preferably avoided. Furthermore, the high toxicity may limit the applicability of cadmium chalcogenide based materials, e.g. in in-vivo imaging. In addition to a low toxicity, a cost-efficient production at an industrial scale can also be considered highly advantageous when scaling the use of nanocrystals from an academic setting to commercial product applications.

Cadmium-free alternatives for manufacturing quantum dots are known in the art, such as $CuInS_2$ and InP. Particularly indium phosphide (InP) QDs are known that have emission characteristics similar to CdSe QDs, while advantageously having a lower toxicity. Methods for colloidally manufacturing InP nanocrystals are known in the art. For example, a first group of known synthesis methods may use a highly reactive phosphorous precursor, e.g. P(−III) as tris(trimethylsylil)phosphine $(TMS)_3P$ or phosphine $PH_3$. A second group of known synthesis methods may use a phosphorous precursor with a lower reactivity, e.g. P(0) or P(+III) as trioctylphosphine TOP, $P_4$ or $PCl_3$. Highly reactive precursors may provide a better size dispersion, which may be an important parameter to obtain QD dispersions suitable for optical devices.

Particularly $(TMS)_3P$ may be commonly used as phosphorous precursor, as it may offer good quality in terms of the properties of the resulting InP nanocrystals. However, this compound may have some disadvantages, e.g. a relatively high cost, pyrophoricity and the production of $PH_3$ in contact with air, which is a highly toxic gas. These disadvantages may also hamper the production of InP nanocrystals at an industrial scale. $PH_3$-based synthesis may also give good results in terms of size dispersion, but has the disadvantage of the high toxicity of $PH_3$. Therefore, $PH_3$ may also be difficult and expensive to use for QD production at a larger scale.

While phosphorous precursors with a low reactivity may provide a less than optimal size dispersion in accordance with synthesis methods known in the art, e.g. may produce nanocrystals with a large size-dispersion which may be difficult to use for various potential applications, these precursors have the advantage of being cheap and easy to use. Synthesis methods known in the art using such low reactivity phosphorous precursors may rely on a two-step method, e.g. in which at least the indium precursor is reduced before reacting with the phosphorous precursor. For example, $InCl_3$ can be reduced by $KBH_4$ to form $In^0$ that reacts with $P^0$, or $InCl_3$ can be reduced by LiR before reacting the $In^0$ with TOP by a catalytic cleavage at high temperature.

The Unites States patent application US 2014/084212 discloses a method for synthesizing InP nanoparticles using an indium trichloride anhydride as an indium raw material and tris(dimethylamino)phosphine $(DMA)_3P$ as a phosphorus raw material. This method includes a preparation step of mixing the indium raw material, the phosphorus raw material, an organic solvent having a boiling point of 170° C. or higher, and an aliphatic amine having a carbon number of 18 or more as a particle surface ligand to obtain a mixture solution, and a synthesis step of synthesizing the InP nanoparticles by heating the mixture solution to 150° C. or higher, but lower than 170° C. $(DMA)_3P$ is a low-reactive phosphorous precursor (P(+III)) which is stable under air, and may cost considerably less than $(TMS)_3P$.

Song et al. also have disclosed a related method for the manufacture of InP QDs in Nanoparticle Res. 15, pp. 1750. With this protocol, InP/ZnS core/shell nanoparticles may be produced with an acceptably low size dispersion. For colloidal semiconductor QDs, the size dispersion is in general directly reflected in the width of the emission spectrum. Song et al. reported InP QDs with a full width at half maximum (FWHM) of 60-65 nm, which may be considered close to the 40-60 nm range of FWHM obtainable with $(TMS)_3P$. Therefore, this method of InP QDs synthesis may combine the advantages of low-reactive phosphorous precursors with good size dispersion.

It is also known in the art to tune the size of the colloidal nanocrystals that are produced, such as to obtain the desired optical and/or electronic properties. A known method to obtain different sizes is to stop the nanocrystals growth during the synthesis. However, a disadvantage of this approach is that the chemical yield for small nanocrystals sizes can be very low because the reaction is not complete. However, methods for high yield size-tuning are also known in the art for synthesis of CdSe or CdS nanocrystals by varying the concentration of the precursors and/or the solute solubility accordingly.

SUMMARY OF THE INVENTION

It is an object of embodiments of the present invention to provide an efficient and/or cheap method for size-tunable production of nanoparticles.

The above objective is accomplished by a method and device according to the present invention.

It is an advantage of embodiments of the present invention that nanocrystals, e.g. InP or InAs nanocrystals, can be efficiently and cheaply manufactured. It is a further advantage of embodiments that nanocrystals, e.g. InP or InAs nanocrystals, can be manufactured that have a low dispersity, e.g. having a full width at half maximum of the emission spectrum in the range of 45 to 60 nm, or even lower. It is an advantage of embodiments of the present invention that nanocrystals can be manufactured that have a good size dispersion.

It is an advantage of embodiments of the present invention that a simple and cheap synthesis can be achieved for high volume production of luminescent materials. For example, the synthesis cost of nanocrystals, such as InP nanocrystals, can be reduced by at least a factor 2, e.g. a factor 3, e.g. at least a factor 4, in comparison to a commonly used synthesis method using a $(TMS)_3P$ precursor.

It is an advantage of embodiments of the present invention that synthesis of nanocrystals can be achieved without requiring cadmium in the process, e.g. a low cost and easily scalable synthesis of Cd-free nanocrystals is achieved.

It is an advantage of embodiments of the present invention that the production of nanocrystals, e.g. InP or InAs nanocrystals, of different sizes, e.g. of a predetermined yet selectable size range, can be performed by a cost-efficient and easily scalable synthesis process.

It is an advantage of embodiments of the present invention that nanocrystals, e.g. InP or InAs nanocrystals, can be synthesized by a full chemical yield reaction, e.g. that an actual yield can be achieved that is at least 70%, e.g. at least 80%, for example 85% or more, e.g. 90%, or even 95% or higher, such as 99%, for example substantially 100%, of the theoretical yield, e.g. when expressing the theoretical yield and the actual yield in terms of moles of the nanocrystal material synthesized. The chemical yield may for example be defined as the percentage of an initially used indium precursor that is converted into InP at the end of the reaction.

It is an advantage of embodiments of the present invention that the synthesis of nanocrystals, e.g. InP nanocrystals, can be size-tuned, e.g. that size-tuned synthesis can be achieved by a full chemical yield reaction, e.g. a substantially full chemical yield as described hereinabove.

It is an advantage of embodiments of the present invention that the synthesis of nanocrystals can be achieved by a full chemical yield reaction without requiring an additional catalyst for enabling or promoting the reaction.

It is an advantage of embodiments of the present invention that a good size dispersion can be achieved, e.g. a narrow particle size range, over a wide range of tunable particle sizes.

The present invention relates to a method for synthesizing nanoparticles, the method comprising:
mixing a first precursor material comprising a first compound comprising a halide moiety and a metal or a metalloid, a second precursor material comprising a second compound comprising at least a polyatomic nonmetal, and a solvent to obtain a mixture solution, and heating said mixture solution such as to colloidally form nanoparticles comprising said polyatomic nonmetal and said metal or comprising said polyatomic nonmetal and said metalloid, wherein said halide moiety is selected such as to colloidally form said nanoparticles in a predetermined size range that is at least partially determined by said halide moiety and wherein an abundance of at least 2.5, preferably at least 4, of the polyatomic nonmetal relative to the metal or the metalloid is obtained in said mixture solution.

It is an advantage of embodiments of the present invention that nanoparticles with a predetermined size can be reached at the final, e.g. highest or best possible, reaction yield.

The second precursor material may comprise a second compound consisting of said at least a polyatomic nonmetal and an amine.

Said mixing may comprise mixing said first precursor material comprising a plurality of different halide moieties, and wherein the relative abundances of said plurality of different halide moieties is selected such as to colloidally form said nanoparticles in a predetermined size range at least partially determined by said relative abundances of the plurality of different halide moieties.

The metal or the metalloid may comprise at least one of cadmium, mercury, zinc, titanium, aluminum, gallium, indium, thallium, silicon, germanium, tin, lead, arsenic, antimony, bismuth, tellurium, polonium or astatine and/or wherein the polyatomic nonmetal comprises phosphorus, sulfur or selenium.

The amine may comprise an aliphatic primary or secondary amine, such as a primary or secondary alkylamine. In some embodiments of the present invention, the aliphatic primary or secondary amine may be one or a combination of dimethylamine, dipropylamine, diethylamine, dibutylamine, dioctylamine, butylamine, octylamine, dodecylamine or oleylamine.

The second precursor material may comprise a phosphorous material. In one example, the second precursor may comprise tris(diethylamino)phosphine, tris(diethylamino) arsine or a combination thereof.

The first precursor material may comprise an indium halide and said second precursor material may comprise tris(diethylamino)phosphine, tris(diethylamino)arsine or a combination thereof.

The method may furthermore comprise a step of degassing the mixture solution before or during said heating.

The heating may be performed under an inert atmosphere.

The mixing may comprise mixing at least one further precursor material in said mixture solution, wherein the at least one further precursor material may comprise at least one further compound comprising a halide moiety and a further metal or metalloid, said further metal or metalloid being different from said metal or said metalloid in the first compound. It is an advantage of embodiments of the present invention that particles with a predefined size can be obtained at final, e.g. full, yield. Said heating may comprise heating said mixture solution such as to colloidally form nanoparticles comprising said polyatomic nonmetal and said metal or metalloid of the first compound, said further metal or metalloid of the at least one further compound and said polyatomic nonmetal.

The first precursor material may comprise indium halide, the second precursor material may comprise tris(diethylamino)phosphine, tris(diethylamino)arsine or a combination thereof, and said at least one further precursor material may comprise a group II metal halide, e.g. a zinc halide.

Mixing the mixture solution and heating the mixture solution may comprise one or both of heating the solvent and injecting the first precursor material and the second precursor material at a predetermined temperature of the solvent. According to embodiments of the present invention the order of heating up and hot injection can be interchanged in order.

Mixing the mixture solution and heating the mixture solution may comprise one or both of heating the solvent mixed with one of the first precursor material and the second precursor material, and injecting the other of the first precursor material and the second precursor material at a predetermined temperature. According to embodiments of the present invention the order of heating up and hot injection can be interchanged in order.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

In a first aspect, the present invention relates to a method for synthesizing nanoparticles comprising the step of mixing a first precursor material comprising a first compound comprising a halide moiety and a metal or a metalloid, a second precursor material comprising a second compound comprising at least a polyatomic nonmetal, and a solvent. The method also comprises the step of heating the mixture such as to colloidally form nanoparticles comprising the polyatomic nonmetal and the metal or comprising the polyatomic nonmetal and the metalloid. In this method, the halide moiety is selected such as to colloidally form the nanoparticles in a predetermined size range that is at least partially determined by this halide moiety. It is an advantage that the size of the colloidal particles can be tuned accurately. In some embodiments, the second precursor material comprises an amine and a polyatomic non-metal and the abundance of the polyatomic nonmetal relative to the metal or the metalloid is obtained of at least 2.5, preferably at least 4, in a mixture solution. It is an advantage of embodiments of the present invention that a high yield can be obtained.

Figure 1:
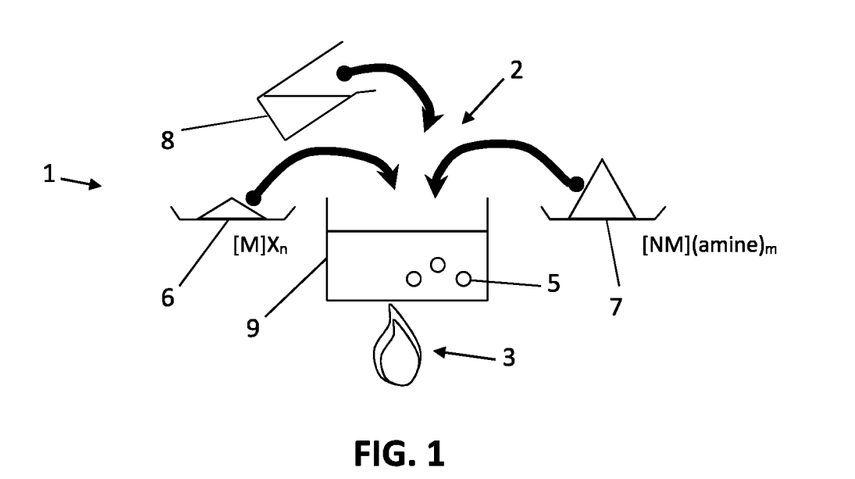
FIG. 1 shows an exemplary method according to embodiments of the present invention.

Referring to FIG. 1, an exemplary method 1 according to embodiments of the present invention for synthesizing nanoparticles 5, e.g. for colloidal synthesis of nanoparticles, is schematically shown. This method comprises a step of mixing 2 a first precursor material 6, a second precursor material 7 and a solvent 8 to obtain a mixture solution 9. For example, the first precursor material and the second precursor material may be dissolved in the solvent to obtain the mixture solution.

The first precursor material 6 comprises a first compound that comprises a halide moiety and a metal or a metalloid. For example, the metalloid may comprise at least one of cadmium, mercury, zinc, titanium, aluminum, gallium, indium, thallium, silicon, germanium, tin, lead, arsenic, antimony, bismuth, tellurium or polonium. The first compound may for example have a structural formula $MX_n$, e.g. MX, $MX_2$ or $MX_3$, where M is a metal or metalloid, such as indium, and X is a halide such as to form a fluoride, chloride, bromide, iodide or astatide material. The first precursor material may also comprise a mixture of different halide compounds comprising the metal or metalloid and/or may comprise a compound of the metal, or the metalloid, and at least two different halides, e.g. $InBrCl_2$ or $InBr_2Cl$.

The second precursor material 7 comprises a second compound comprising at least a polyatomic non-metal. According to some advantageous embodiments, the second compound may consist of one or more amines and a polyatomic non-metal. The polyatomic nonmetal may comprise phosphorus, arsenide, antimony, sulfur, tellurium or selenium. In embodiments wherein the second compound comprises an amine (which may in this context also be referred to as an amine group), the amine may be an aliphatic primary or secondary amine, such as a primary or secondary alkylamine. Examples thereof are given by a dimethylamine, dipropylamine, diethylamine, dibutylamine, dioctylamine, butylamine, octylamine, dodecylamine or oleylamine. In such embodiments, the second compound may for example have a general chemical formula of $A(NR_2)_m$, wherein A is a polyatomic nonmetal and wherein each $NR_2$ is independently an amine as earlier described. It is an advantage of such compound of an amine and a polyatomic non-metal that an economic synthesis can be obtained. For example, a common precursor such as $(TMS)_{3P}$ may cost 56 k€/mol, while a precursor in accordance with embodiments of the present invention such as tris(dimethylamino)phosphine $(DMA)_3P$ may cost 1.6 k€/mol. Furthermore, in a prior-art method, chemical yields may be obtained of about 20%, whereas in a method according to embodiments of the present invention a chemical yield in the range of 70% to 100%, e.g. of 80% to 100%, may be obtained.

In embodiments according to the present invention, the second precursor material may comprise a tris(dimethylamino)phosphine $(DMA)_3P$. In embodiments according to the present invention, the second precursor material may comprise a tris(diethylamino)phosphide $(DEA)_3P$. It is an advantage of $(DEA)_3P$ that it is a relatively cheap product, it has advantageously a boiling point, e.g. about 240° C., that is higher than an exemplary synthesis temperature of InP, e.g. about 180° C., and furthermore has an advantageously high concentration of phosphorus, such that only a small volume of the precursor needs to be injected in the reaction mixture. In yet other embodiments according to the present invention, the second precurusor material may comprise a tris(diethylamino)arsine and, optionally, a tris(diethylamino)phosphide.

Embodiments of the present invention may relate to a method wherein a tris(amino)phosphine and/or tris(amino)arsine precursor, generally referred to as $P(amino)_3$ and/or $As(amino)_3$, and an indium halide precursor, referred to as $InX_3$, are used.

For example, in embodiments according to the present invention, the first precursor material may comprise an indium halide, such as indium fluoride, indium bromide, indium chloride or indium iodide, and the second precursor material may comprise tris(diethylamino)phosphine, tris(diethylamino)arsine or a combination thereof.

The solvent 8 may comprise a coordinating solvent, e.g. an amine such as a primary amine, for example oleylamine, dodecylamine or octylamine. The solvent 8 may also comprise a mixture of a non-coordinating solvent, such as octadecene, and at least one amine, such as a primary amine.

The step of mixing 2 may also comprise mixing at least one further precursor material comprising at least one further compound in the mixture solution. This at least one further compound may comprise a halide moiety, e.g. the same halide moiety or a different halide moiety as in the first compound, and a further metal or metalloid, where this further metal or metalloid is different from the metal or the metalloid in the first compound.

The first precursor material 6, the second precursor material 7 and the solvent 8 may be mixed such as to obtain a mixture solution 9 in which an abundance of the polyatomic nonmetal relative to the metal, or an abundance of the polyatomic nonmetal relative to the metalloid, is obtained of at least 2.5, for example an abundance of at least 3 times, e.g. at least 4 times, e.g. at least 5 times, for example at least 10 times, the amount of polyatomic non-metal relative to the amount of the metal or the metalloid may be mixed in the mixture solution. This abundance, which may also be called 'molar ratio', is expressed as the ratio of moles of the polyatomic non-metal over moles of the metal or metalloid obtained in the mixture solution 9. It is an advantage of embodiments of the present invention that a full chemical yield, e.g. conversion of at least 70%, e.g. at least 80%, of the metal or metalloid cation in the first precursor into nanoparticles can be achieved. For example, an abundance of at least 2.5 typically leads to a chemical yield of at least 60%, whereas an abundance of at least 4 typically leads to a chemical yield of sufficiently 100%. This chemical yield can be defined as the percentage of the initially used metal or metalloid precursor, e.g. an indium precursor, that is converted into InP at the end of the reaction. This advantage may be achieved by adding an excess on the second precursor material, e.g. of a phosphorous precursor such as $(DEA)_3P$ to obtain a high yield. This second precursor may generally be considerably cheaper than the first precursor. Therefore, economically attractive synthesis of nanoparticles, such as InP nanocrystals can be achieved. For example, where InP nanocrystals may be produced in accordance with a prior-art method in which a chemical yield of about 20%, for example having a synthesis cost of about 180 €/g associated therewith, InP nanocrystals may be produced in accordance with embodiments of the present invention with a chemical yield of 85%, for example having an estimated synthesis cost of about 60 €/g, e.g. achieving a 66% reduction of the cost.

The method 1 further comprising heating 3 the mixture solution such as to colloidally form nanoparticles 5. It shall be clear to the person skilled in the art that this step of heating may be performed after obtaining the mixture solution, or while obtaining the mixture solution, e.g. the solvent may be heated and the first precursor material and/or the second precursor material may be added to the heated solvent. The temperature can for example be tuned between 100° C. to 300° C.

Heating 3 the mixture may comprise heating the mixture solution such as to colloidally form nanoparticles comprising the polyatomic nonmetal and the metal or metalloid of the first compound, the further metal or metalloid of the at least one further compound, in embodiments where such at least one further precursor is added to the solution, and the polyatomic nonmetal.

The method 1 may also comprise a degassing step before or during heating of the mixture solution. Alternatively, the method may not require a degassing step. The step of heating 3 may be performed under an inert atmosphere.

The nanoparticles thus formed comprise the polyatomic nonmetal and the metal or the metalloid. For example the nanoparticles may comprise InP nanoparticles, InP/ZnS core/shell nanoparticles, InAs nanoparticles, CdSe nanoparticles, CdS nanoparticles, HgTe nanoparticles, or other such nanoparticles known in the art.

Furthermore, the halide moiety in the first compound of the first precursor material 6 is in accordance with embodiments of the present invention selected such as to colloidally form these nanoparticles in a predetermined size range that is at least partially determined by the halide moiety.

The first precursor material may comprise a plurality of different halide moieties. The relative abundances of this plurality of different halide moieties may be selected such as to colloidally form the nanoparticles in a predetermined size range at least partially determined by their relative abundances.

By changing the inorganic moieties linked to the metal or metalloid cation, size tuning can be achieved, e.g. at substantially full chemical yield. For example a chemical yield, as defined hereinabove, may be achieved of at least 70%, or of at least 80%.

While it may be known in the art to stop the growth of nanoparticles during synthesis, in such method, the chemical yield can be very low because the reaction is not complete. For example, the size of the nanocrystals may generally increase over time during synthesis. If the synthesis is stopped before the nanocrystals achieve their maximum size, smaller nanocrystals can be obtained. However, in such case, as the reaction is stopped before its end, the chemical yield is also smaller than the chemical yield obtained for the maximum nanocrystals size. Furthermore, increasing the precursor concentration may lead to difficulties to solubilize the solid precursors while decreasing the precursor concentration may lead to higher size dispersion.

Embodiments of the present invention may enable the production of nanoparticles in a predetermined size range, e.g. enable size-tuning, while achieving a substantially higher yield. Therefore, in accordance with embodiments of the present invention, the production of nanocrystals of different sizes can be easily achieved by changing the precursor halides.

Furthermore, the size range of the nanoparticles can be further tuned by varying the concentrations of the precursors. Where a first, coarse grained size-tuning can be achieved by selecting the halide group of the precursor accordingly, as described hereinabove, a finer grained size-tuning can be achieved by further tuning the concentrations of the precursors. Therefore, a wider range of particle sizes can be achieved without the disadvantages of solubility difficulties at high precursor concentrations and large size dispersion at low precursor concentrations.

For example, at high precursor concentrations, the critical size at which the nanoparticles neither grow nor shrink may be relatively small. Therefore, smaller particles may grow faster than large particles, since larger crystals would require more atoms to grow in diameter. Over time, the precursor concentration diminishes, and the critical size increases. This may result in a convergence of the size distribution, yielding a substantially monodisperse particle distribution of predetermined size when the synthesis is substantially completed.

For example, in accordance with embodiments of the present invention, size tuning of InP particles while maintaining substantially full chemical yield conditions can be achieved for nanoparticles with InP core sizes between 2.3 nm and 3.5 nm. Furthermore, a larger range of sizes may be obtained by changing the concentration of the precursors. For example, smaller sizes may be obtained by increasing the phosphorous, indium and zinc precursors concentrations, while larger sizes may be obtained by reducing the phosphorous, indium and zinc precursors concentrations.

It is a further advantage of a method according to embodiments of the present invention that the predetermined size range of the nanoparticles may correspond to the maximum particle size range obtainable by the synthesis reaction given the halide or halides used and the concentrations of the precursors. Therefore, the synthesis can be carried out without requiring a time-sensitive step of stopping the reaction, thus imposing less stringent requirements on process control.

In a first example, embodiments of the present invention not being limited thereby, InP nanocrystals are synthesized. The size can be tuned by selecting the indium and/or zinc halides. Sizes are reported hereinbelow in terms of particle diameter of the nanocrystals, and are determined using the spectral position of the first excitonic absorption peak in the absorption spectrum of the nanocrystals solution, as is known in the art.

In this example, InP nanoparticles, e.g. InP nanocrystals, were synthesized with an exciton energy of 580 nm, corresponding to an estimated diameter of 3.3 nm. 100 mg (0.45 mmol) of indium(III) chloride, as indium raw material, and 300 mg (2.2 mmol) of zinc(II) chloride, as zinc raw material, are mixed in 5.0 mL (15.2 mmol) of technical oleylamine, which is a coordinating solvent. The reaction mixture is stirred and degassed at 120° C. for an hour and then quickly heated to 180° C. under inert atmosphere. Upon reaching 180° C., a volume of 0.40 mL (1.46 mmol) of tris(diethylamino)phosphine is quickly injected in the above mixture. This results in a phosphorous:indium ratio of 3.2:1. After the phosphorous precursor injection, synthesis of InP nanocrystal occurs. This reaction may for example occur during 30 minutes. At the end of the reaction, the temperature is lowered, e.g. the mixture is cooled down. InP nanocrystals are then precipitated in ethanol and suspended in chloroform. This synthesis provides InP nanocrystals with a diameter of 3.3 nm, corresponding to a first excitonic absorption peak at 580 nm.

Likewise, 3.0 nm InP nanocrystals are obtained, corresponding to a first excitonic absorption peak at 560 nm, when using indium(III) bromide and zinc(II) chloride as the metal cation precursor and the same concentrations and protocol as described hereinabove. 2.8 nm InP nanocrystals are obtained, corresponding to a first excitonic absorption peak at 520 nm, when using indium(III) iodide and zinc(II) chloride. 2.4 nm InP nanocrystals are obtained, corresponding to a first excitonic absorption peak at 440 nm, when using indium(III) bromide and zinc(II) bromide. 2.3 nm InP nanocrystals are obtained, corresponding to a first excitonic absorption peak at 420 nm, when using indium(III) iodide and zinc(II) iodide.

Furthermore, the nanoparticle sizes can be further tuned by changing the precursor concentrations. 3.0 nm InP nanocrystals, corresponding to a first excitonic absorption peak at 550 nm, may be obtained by doubling the phosphorous, indium and zinc concentrations of the example hereinabove.

Without being bound by theory, a typical reaction scheme for embodiments of the present invention in accordance with this first example may be proposed. This reaction scheme is believed to typically comprise, in a first step, a transamination, i.e. an exchange between the amine used as a solvent (R"NH$_2$, such as oleylamine) in the synthesis and the amino groups coordinating to phosphorus (NR'$_2$, such as NEt$_2$) in the original precursor. The full transamination can be written as a sequence of three successive reactions:

$$P(NR'_2)_3 + R''NH_2 \rightleftharpoons P(NR'_2)_2(NHR'') + R'_2NH \quad (1)$$

$$P(NR'_2)_2(NHR'') + R''NH_2 \rightleftharpoons P(NR'_2)(NHR'')_2 + R'_2NH \quad (2)$$

$$P(NR'_2)(NHR'')_2 + R''NH_2 \rightleftharpoons P(NHR'')_3 + R'_2NH \quad (3)$$

Particularly when the resulting amine side product (R'$_2$NH) is a volatile compound such as dimethylamine or diethylamine, which is easily evacuated from the reaction medium, this equilibrium is shifted towards the fully transaminated aminophosphine. Furthermore, this transamination typically occurs at a much faster rate than the nanoparticle formation. As such the transaminated aminophosphine is typically the prevailing aminophosphine species already within a few seconds after injection. Subsequently, in a further step of the reaction scheme, a redox reaction occurs in which 1 equivalent of InP is formed by the oxidation of 3 equivalents of the transaminated aminophosphine:

$$InX_3 + 4P(NHR'')_3 \xrightarrow{+III \quad -III \quad +V} InP + 3P(NHR'')_4X \quad (4)$$

wherein X is a halogen, such as Cl, Br or I. This final redox reaction allows to rationalize the observed chemical yields (cf. inra).

Comparing a InP nanoparticle synthesis according to embodiments of the present invention to a commonly used synthesis using a (TMS)$_3$P precursor, it is estimated that the synthesis cost may be reduced by a factor of 4 or more. This cost estimation takes present prices of the chemical products into account, but does not account for the simplicity of use of (amino)$_3$P precursors, which may also significantly contribute to large scale synthesis of the nanoparticles at a reasonable price. In a conventional (TMS)$_3$P-based InP synthesis, the phosphorous precursor may be responsible for about 95% of the total cost of the synthesis, as detailed in the tables hereinbelow. In these tables, unit cost expresses an exemplary cost in euro of a unit of the precursor. A chemical yield of 100% was assumed for the exemplary tabulated data for InP synthesis using a (TMS)$_3$P precursor as known in the art, a yield of 20% for InP synthesis using a (DMA)$_3$P precursor as known in the art, and a yield of 80% for the InP synthesis as described in an example hereinabove using a (DEA)$_3$P precursor, according to embodiments of the present invention discussed hereinabove.

| Prior art (TMS)$_3$P-based synthesis | unit cost | units/g InP | cost/g InP |
|---|---|---|---|
| (TMS)$_3$P | 216 €/G | 1.8 | 388.8 |
| Indium Acetate | 5 €/G | 2 | 10 |
| Octadecene | 40 €/L | 0.1 | 4 |
| Methanol | 50 €/L | 0.3 | 15 |
| Total Cost | | | € 417.8 |

| Prior-art (DMA)$_3$P-based synthesis | unit cost | units/g InP | cost/g InP |
|---|---|---|---|
| P(DMA)$_3$ | 7.1 €/G | 8.6 | 60.8 |
| Indium Chloride | 12.1 €/G | 7.6 | 91.6 |
| Oleylamine | 160 €/L | 190.5 | 30.5 |
| Ethanol | 23 €/L | 381.1 | 8.8 |
| Total Cost | | | € 191.6 |

| (DEA)$_3$P-based synthesis | unit cost | units/g InP | cost/g InP |
|---|---|---|---|
| P(DEA)$_3$ | 5.9 €/G | 6.9 | 40.3 |
| Indium Chloride | 12.1 €/G | 1.9 | 22.9 |
| Oleylamine | 160 €/G | 95.3 | 15.2 |
| Ethanol | 23 €/G | 190.5 | 4.4 |
| Total Cost | | | € 82.8 |

It may be known in the art to replace a (TMS)$_3$P phosphorous precursor by (DMA)$_3$P, which is an (amino)$_3$P type precursor, thereby allowing a reduction of the synthesis cost. For example, (DMA)$_3$P may be about 30 times cheaper than (TMS)$_3$P. However, (DEA)$_3$P may be even cheaper. Furthermore, the chemical yield of the reaction has also to be taken into account to estimate the total cost of the synthesis. The chemical yield is defined as the percentage of the initially used indium precursor that is effectively converted into InP nanocrystals at the end of the reaction. The chemical yield is estimated by measuring the absorbance of a known dilution of the reaction mixture in the short wavelength range. The dilution is estimated by first measuring the mass of the aliquot withdrawn from the mixture. Then a known volume of toluene is added to the aliquot. The absorbance of the provided solution is then measured. It is well-known that the intrinsic absorption coefficient of colloidal nanocrystals are close to those of bulk materials in the short wavelength range. Knowing the intrinsic absorption coefficient of bulk InP, these values are then used to calculate the chemical yield of InP nanocrystals solution.

For example, an aliquot with a measured mass $m_{aliquot}$=20 mg is withdrawn from the reaction mixture, e.g. where the total mass of the reaction mixture is $m_{Total}$=4.5 g. 3.0 mL of toluene is added with the aliquot to an absorbance cuvette. An absorbance A of 0.45 is measured at $\lambda$=413 nm for the aliquot toluene solution. As known in the art, the intrinsic absorption coefficient is given by:

$$\mu_{i,th} = \frac{4\pi nk|f_{LF}|^2}{n_S \lambda}$$

where n and k are the real and imaginary part of the refractive index of bulk zinc-blende InP. and $n_S$ is the refractive index of toluene. The local field factor $f_{LF}$ is given by:

$$|f_{LF}|^2 = \frac{9n_S^4}{(n^2 - k^2 + 2n_S^2)^2 + 4(nk)^2}$$

For n, k and $n_s$, appropriate values are known in the art, for example, at $\lambda$=413 nm: n=4.395, k=1.247, $n_s$=1.52. Then $|f_{LF}|^2$=0.078 and $\mu_{i,th}$=8.5·10$^6$ m$^{-1}$.

Therefore, the volume fraction f of InP in the aliquot can be deduced using the measured absorbance A and the theoretical intrinsic absorption coefficient $\mu_{i,th}$:

$$f = \frac{A \cdot \ln(10)}{\mu_{i,th} \cdot L} = 1.2 \cdot 10^{-5}$$

Where L is the cuvette length (m). The amounts of InP units can then be deduced from f and InP molar volume $V_M$.

$$n_{cuvette} = f \cdot \frac{V_{cuvette}(m^3)}{V_M\left(\frac{m^3}{mol}\right)} = 1.2 \cdot 10^{-5} \cdot \frac{3.0 \cdot 10^{-6}}{3.0 \cdot 10^{-5}} = 1.2 \cdot 10^{-6} \text{ mol}$$

The total amount of InP units in the reaction mixture can be calculated with the ratio between the mass of the aliquot $m_{aliquot}$ and the mass $m_{Total}$ of the reaction mixture.

$$n_{Total} = n_{cuevette} \cdot \frac{m_{Total}}{m_{aliquot}} = 1.2 \cdot 10^{-6} \cdot \frac{4.5}{20 \cdot 10^{-3}} = 0.27 \text{ mmol}$$

Defining the chemical yield C.Y. as a percentage of InP units in the reaction mixture $n_{Total}$ and the In quantity $n_{In}$ that was initially put in the reaction mixture, one obtains a yield of:

$$C.Y. = \frac{n_{Total}}{n_{In}} \cdot 100 = \frac{0.27}{0.45} \cdot 100 = 60\%$$

Therefore, for this illustrative example, a chemical yield of 60% is obtained, e.g. 60% of the initially used indium precursor has been effectively converted into InP nanocrystals at the moment of the reaction we have taken the aliquot. However, this is merely an illustrative example for describing the method used for determining the chemical yield in examples of embodiments of the present invention described herein, wherein the yield obtainable by a method according to embodiments may be significantly higher than the present illustrative example.

Figure 8:
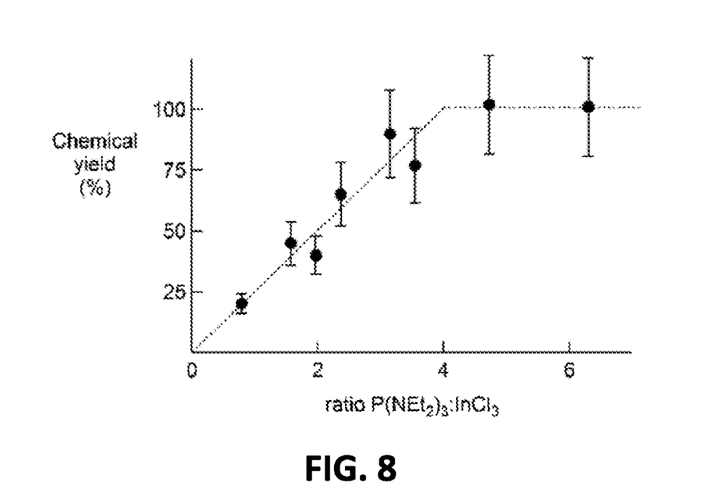
FIG. 8 shows the obtained chemical yield as function of the P:In ratio, in accordance with embodiments of the present invention.

Thus, in accordance with this illustrative example, the chemical yield of InP nanocrystals synthesis according to prior art methods and according to embodiments of the present invention can be determined and compared. An example is shown in FIG. 8, wherein the obtained chemical yield is plotted in function of the ratio of P(NEt2)3 to InCl3, corresponding to the P:In ratio or abundance, in accordance with embodiments of the present invention; wherein the dotted line is merely meant to guide the eye. If a 1:1 P:In ratio is used with (Amino)$_3$P, a chemical yield of 10-30% is measured. This already leads to a cost reduction of the synthesis by more than a factor 2 in comparison to the (TMS)$_3$P based synthesis, as shown hereinabove. To increase the chemical yield of the synthesis, a higher P:In ratio is selected in accordance with embodiments of the present invention. For instance, in the case of (DEA)$_3$P, another (Amino)$_3$P precursor, a P:In ratio of 3.3:1 may result in a chemical yield in the range of 75% to 85%. These observed chemical yields are in accordance with the proposed reaction scheme, wherein a P:In ratio of 4:1 is needed to allow a full yield for the redox reaction (eq. 4). The chemical yield has a large impact on the cost of the synthesis. For example, as shown hereinabove, a cost reduction of more than a factor 2 is estimated between a 20% chemical yield synthesis and an 80% chemical yield synthesis.

While adding an excess of the (DEA)$_3$P precursor results in a certain quantity of the (DEA)$_3$P not reacting, contra-intuitively it is observed that this unconsumed part of the precursor is economically compensated by the high chemical yield of the reaction, e.g. since the cost of the (DEA)$_3$P may be sufficiently low.

Changing the precursor concentration is a possible size-tuning strategy that can be applied for nanoparticle synthesis, where higher precursor concentrations may result in smaller nanocrystals. However, increasing the precursor concentration may lead to difficulties to solubilize the solid precursors, while decreasing the precursor concentration leads to higher size dispersion.

In accordance with embodiments of the present invention, size-tuning can be achieved in a synthesis method at a substantially constant chemical yield, e.g. at a high and substantially constant yield, by changing the halides, e.g. the indium halides. Furthermore, good size dispersion can be achieved over a wide range of tuned particle sizes.

Figure 2:
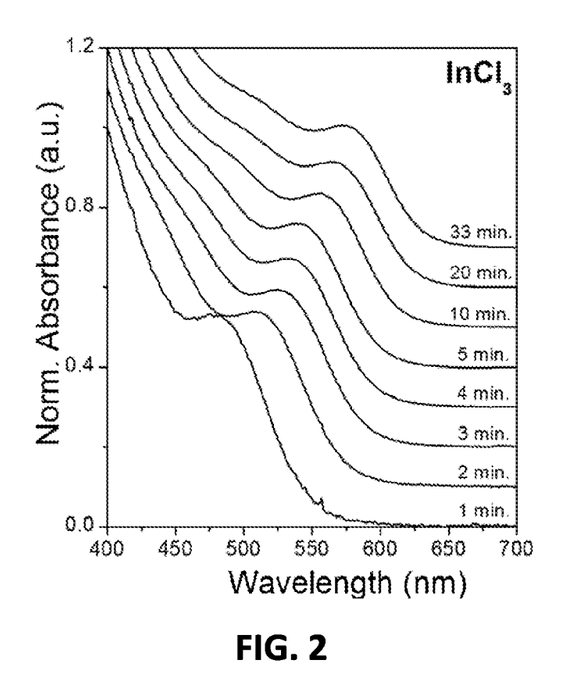
FIG. 2 shows absorption spectra at different times during InP synthesis using $InCl_3$ as indium precursor, in accordance with embodiments of the present invention.
Figure 3:
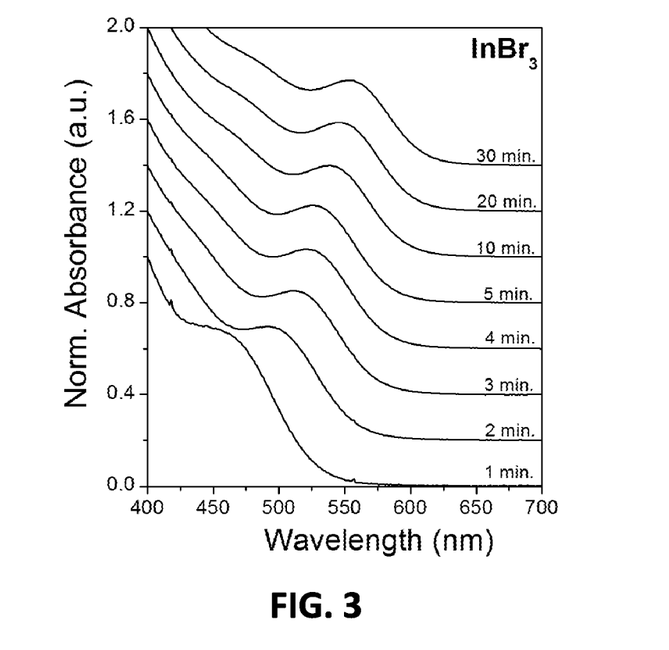
FIG. 3 shows absorption spectra at different times during InP synthesis using $InBr_3$ as indium precursor, in accordance with embodiments of the present invention.
Figure 4:
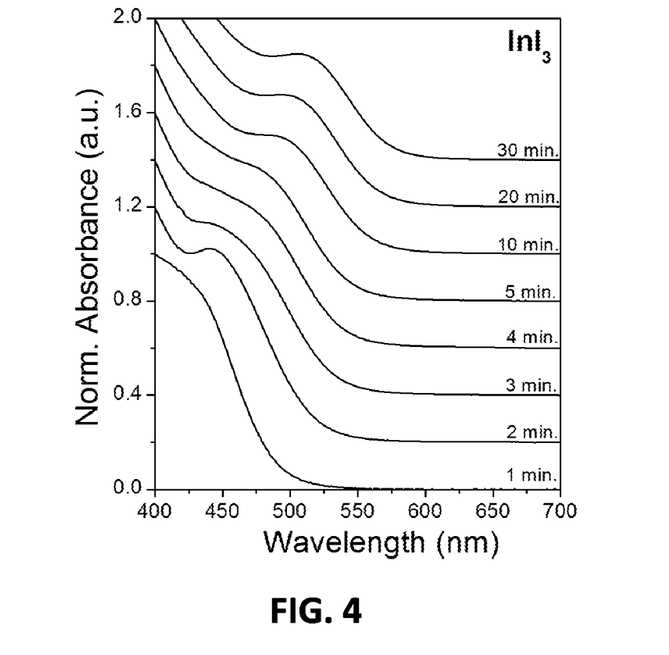
FIG. 4 shows absorption spectra at different times during InP synthesis using $InI_3$ as indium precursor, in accordance with embodiments of the present invention.
Figure 5:
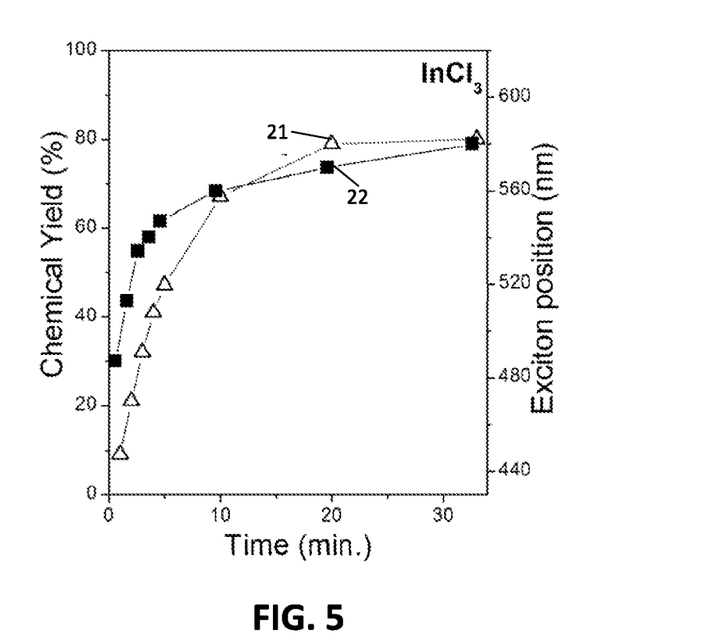
FIG. 5 shows the first exciton spectral position and the associated measured chemical yield for $InCl_3$ as indium precursor, in accordance with embodiments of the present invention.
Figure 6:
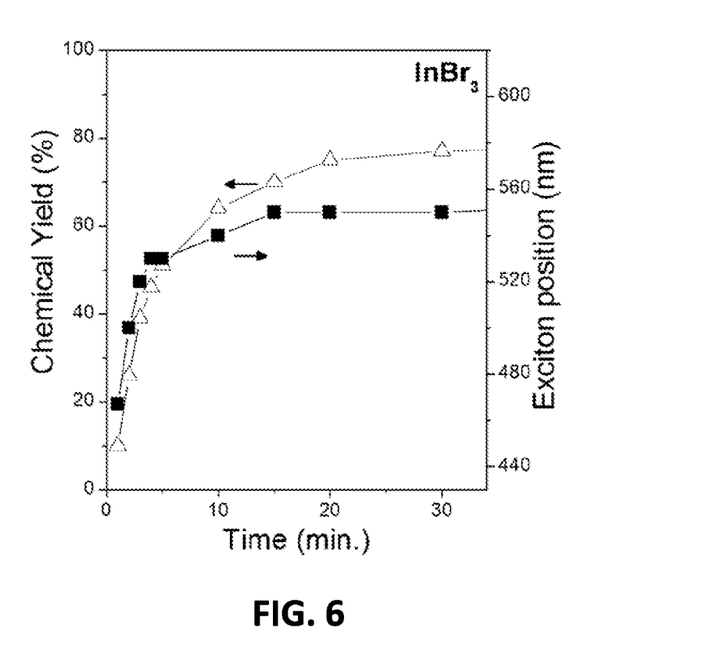
FIG. 6 shows the first exciton spectral position and the associated measured chemical yield for $InBr_3$ as indium precursor, in accordance with embodiments of the present invention.
Figure 7:
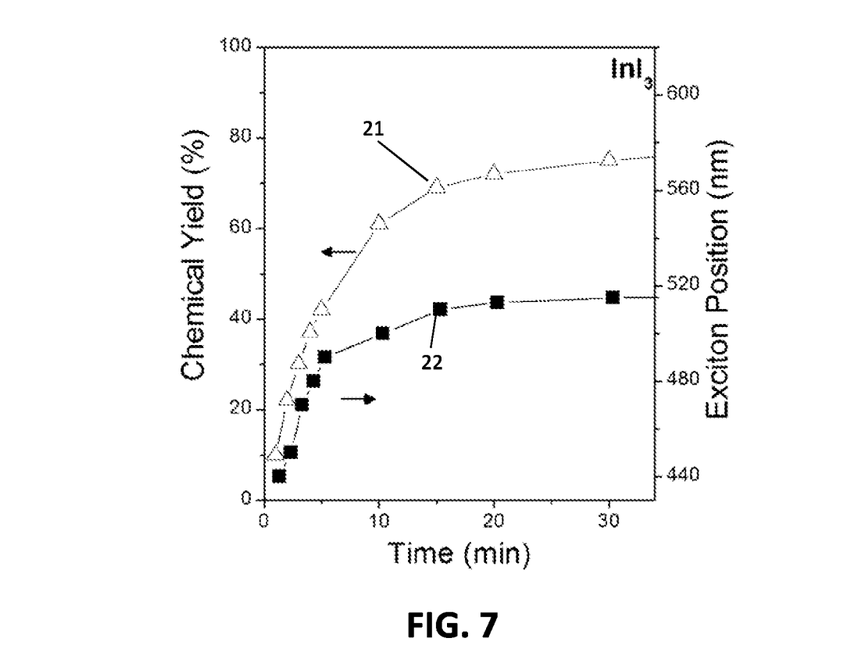
FIG. 7 shows the first exciton spectral position and the associated measured chemical yield for $InI_3$ as indium precursor, in accordance with embodiments of the present invention.

FIG. 2 shows absorption spectra of aliquots taken during different time of an InP synthesis using InCl$_3$ as the indium precursor, in accordance with embodiments of the present invention. FIG. 3 and FIG. 4 show the same type of measurement for InP syntheses using respectively $InBr_3$ and $InI_3$ precursors in accordance with embodiments of the present invention. These three syntheses have been realized under the same conditions. Precursor concentration, solvent, zinc salt nature and quantity, solvent volume, phosphorous precursor quantity are the same between each synthesis, e.g. the only parameter that differs is the halide in the indium halides used. It can be observed that the first exciton spectral position evolution is not the same for these three syntheses. At the same time of reaction the first exciton spectral position is red-shifted with $InCl_3$ as compared to $InBr_3$, while with $InI_3$ it is blue-shifted. The first exciton spectral positions 22 and the associated measured chemical yield 21 for $InCl_3$, $InBr_3$ and $InI_3$ precursors are respectively plotted in FIG. 5, FIG. 6 and FIG. 7. It can be seen that for these three syntheses, the final chemical yield is high, e.g. in the range of about 75% to about 80%. However the final first exciton spectral position is different, which is characteristic of different sizes. Using $InCl_3$, $InBr_3$ and $InI_3$ the final exciton position is respectively 580, 560 and 515 nm. This clearly shows that size-tuning can be achieved by simply replacing the indium precursor in the synthesis. Thus, size-tuning at high chemical yield is demonstrated for InP nanocrystals, which may be achieved by changing inorganic moieties linked to the metal cation precursor in accordance with embodiments of the present invention.

If $InCl_3$ or $InBr_3$ or $InI_3$, were to be used with acid compounds as carboxylic acid, these groups that contain labile hydrogen could replace the halide in the indium complex. This would lead to the formation of HCl, respectively HBr or HI, and indium(carboxylate)$_3$. In such case, the influence of the halides on the InP synthesis is considerably reduced, even though it may not be fully eliminated. However, in accordance with embodiments of the present invention, $InX_3$ (X: halide) is mixed with amines. Amines are bases, and consequently HX formation is not favored in this case. Therefore, the halides remain close to the indium, and thus can have a possible significant influence in the nucleation/growth process. In the same way, size-tuning at high chemical yield can also be obtained by changing the zinc halides. As was already mentioned, $ZnCl_2$ is used to obtain a better size dispersion and to start the shell growth in this method. If $ZnBr_2$ or $ZnI_2$ are used instead of $ZnCl_2$, a size effect is also observed, as shown in the table hereinbelow. Following table indicates the InP quantum dot sizes obtained at full chemical yield in terms of the exciton energy (in nm) and the exciton linewidth between brackets (in nm).

|  | Zn dihalides | | |
| --- | --- | --- | --- |
| Indium trihalides | $ZnCl_2$ (2.2 mmol) | $ZnBr_2$ (2.2 mmol) | $ZnI_2$ (2.2 mmol) |
| $InCl_3$ (0.45 mmol) | 580 (48) | 515 (51) | 420 (>80) |
| $InBr_3$ (0.45 mmol) | 550 (50) | 450 (>80) | 410 (>80) |
| $InI_3$ (0.45 mmol) | 520 (54) | 440 (>80) | 400 (>80) |

For example, using $InCl_3$ with $ZnBr_2$ instead of $ZnCl_2$ leads to InP nanocrystals with an exciton energy of 515 nm instead of 580 nm at the end of the reaction. The smallest reported sizes were obtained with a mixture of $InI_3$ and $ZnI_2$. As in the case of indium halides, moving for more electronegative halides leads to smaller sizes. However, changing the zinc halides leads to a higher dispersity in comparison of changing the indium halides, as shown in the table hereinabove.

While size-tuning may already be known in the art for CdSe nanocrystals by tuning the reaction rate, e.g. in the case when precursor concentrations are changed. However in the InP synthesis according to present example in accordance with embodiments of the present invention, the size-tuning, e.g. which may be at least partially achieved by changing the indium halides, does not modify the reaction rate. Indeed, reaction half-times with different indium halides remain substantially the same.

The same reaction rate yet different final sizes may already be known for CdSe nanocrystals where size-tuning is achieved by changing the acid quantity added to the reaction mixture. However, in this case, size-tuning may be explained by a modification of the monomer solubility that affects the nucleation takeover and then the nanocrystals final sizes. However, an explanation based on the change of the monomers solubility is unlikely for an InP synthesis in accordance with embodiments. For CdSe nanocrystals, the diameter increases with the monomer solubility. For InP nanocrystals, smallest nanocrystals are obtained with $InI_3$. Yet the solubility in oleylamine of $InI_3$ should be higher than for $InCl_3$ or $InBr_3$. In the series Cl, Br and I, the polarizability of the anion increases. This means that the In—X bond goes from ionic to more covalent. $InI_3$ would therefore be more soluble in a coordinating solvent than in an ionic structure.

If it were to be assumed that the monomer solubility should depend on the In halides solubility, for more soluble indium halides more soluble monomers should be obtained, and thus larger nanocrystals, which is the opposite of that we observe. More importantly in the case of CdSe nanocrystals, an increase of the monomer solubility leads to a larger size dispersion. However, in the case of InP synthesis in accordance with embodiments of the present invention, no significantly larger size-dispersion is observed by changing the halides.

Surprisingly, it appears that the dispersity is slightly lower for the larger sizes. This should be theoretically the opposite when assuming the higher solubility hypothesis.

Furthermore, the halides may play a role of ligand, and may thus affect the nucleation process. Iodide is bigger than the other halides used in the present examples, and may therefore impede the monomer capture by the nuclei. Thus, larger halides could imply a slower monomer adsorption rate. This would result in delaying the nucleation takeover, and may therefore lead to more nuclei and thus to smaller nanocrystals. Likewise, using smaller halides may lead to an earlier nucleation takeover and consequently bigger nanocrystals.

In a second example, InP/ZnSe core/shell nanoparticles were synthesized. In a first step, the InP core was formed, similarly to the first example. 100 mg (0.45 mmol) of indium(III) chloride, as indium raw material, and 300 mg (2.2 mmol) of zinc(II) chloride, as zinc raw material, are mixed in 5.0 mL (15 mmol) of technical oleylamine, which is a coordinating solvent. The reaction mixture is stirred and degassed at 120° C. for an hour and then heated to 180° C. under inert atmosphere. Upon reaching 180° C., a volume of 0.45 mL (1.6 mmol) of tris(diethylamino)phosphine is quickly injected in the above mixture. This results in a phosphorous:indium ratio of 3.6:1. After the phosphorus precursor injection, the InP nanocrystals synthesis proceeded. The InP core QDs reaction occurs during 30 minutes. After 30 minutes, the ZnSe shell growth procedure is started, which consists of 3 cycles of slowly injecting stoichiometric trioctylphosphine selenium (2.2 M), increasing the temperature, slowly injecting Zn(stearate)$_2$ in 4 mL of octadecene and again increasing the temperature. 1 mL of stoichiometric trioctylphosphine selenium (2.2 M) is initially slowly injected after these 30 minutes, followed by 0.7 mL after 150 and 210 min. 1 g of Zn(stearate)$_2$ in 4 mL of octadecene is slowly injected after 120, 180 and 240 min. The temperature, starting at 180° C., is increased by 20° C. after 60, 120 and 150 min and by 40° C. after 180 and 210 min, ending at 320° C. The reaction is finalized after 300 minutes, whereupon the temperature is cooled down. InP/ZnSe nanocrystals are then precipitated in ethanol and suspended in chloroform.

In a third example, InAs nanoparticles were synthesized. 200 mg (0.9 mmol) of indium(III) chloride, as indium raw material, and 400 mg (2.9 mmol) of zinc(II) chloride, as zinc raw material, are mixed in 5.0 mL (15 mmol) of technical oleylamine. The reaction mixture is stirred and degassed at 120° C. for an hour and then heated to 180° C. under inert atmosphere. Upon reaching 180° C., a volume of 0.17 mL (0.9 mmol) of tris(dimethylamino)arsine is quickly injected in the above mixture. After 10 minutes, 0.7 mL (2.7 mmol) of tris(diethylamino)phosphine is slowly injected (drop wise, 0.7 mL in 30 minutes). The reaction is ended after 40 min, after which the temperature is cooled down. InAs nanoparticles are then precipitated in ethanol and suspended in toluene.

Figure 9:
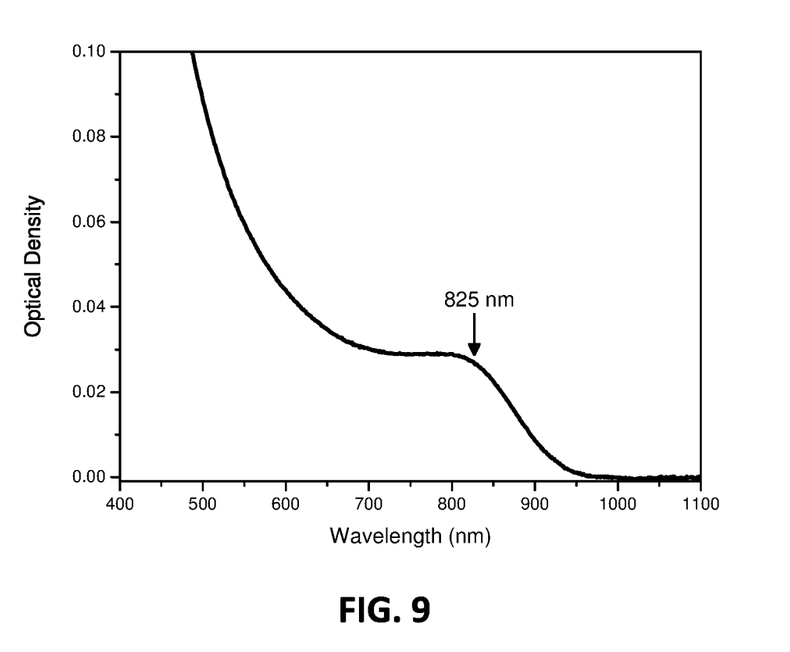
FIG. 9 shows an absorption spectrum of the InAs nanoparticles, in accordance with embodiments of the present invention.
Figure 10:
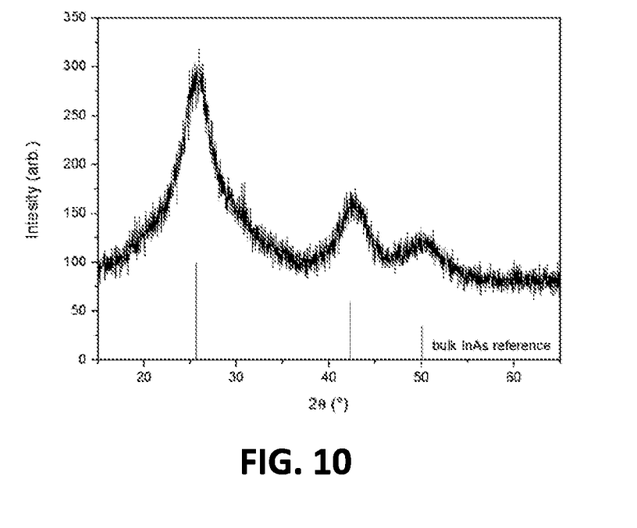
FIG. 10 shows an X-ray diffraction diagram of the InAs nanoparticles, in accordance with embodiments of the present invention.

With reference to FIG. 9, the absorption spectrum of the obtained InAs nanoparticles is provided. Furthermore, an X-ray diffraction diagram of the obtained nanoparticles, in comparison to bulk InAs, is shown in FIG. 10, proving that indeed InAs nanoparticles are formed.

Similarly to the reaction scheme of the first example, without being bound by theory, both the tris(diemthylamino) arsine and the tris(diethylamino)phosphine are believed to undergo transamination as earlier described. Furthermore, the aminoarsine now replace the 1 equivalent of aminophosphine which is reduced in the redox reaction. As such, 1 equivalent of InAs is formed by the oxidation of 3 equivalents of the aminophosphine:

(5)

In conclusion, a method according to the embodiments allows the manufacture of high quality nanoparticles, such as InP, InP/ZnSe or InAs nanocrystals, with cheap and easy-to-use precursors and a substantially full chemical yield of the reaction. By changing the polyatomic nonmetal halides, such as indium halides, the nanoparticle sizes can be tuned while maintaining this high chemical yield. A method according to embodiments may be particularly suitable for the synthesis of cadmium-free colloidal nanocrystals, even though embodiments of the present invention may also be suitable for the cadmium-based synthesis of nanocrystals.

In another aspect, the present invention also relates to a colloidally formed nanoparticle comprising a polyatomic nonmetal and a metal or comprising a polyatomic nonmetal and a metalloid, the nanoparticle being formed using a method as described in the first aspect. Optional features may be as described with respect to the nanoparticles obtained using the methods of the first aspect.

In a third aspect, the present invention relates to a method for synthesizing nanoparticles, the method comprises mixing a first precursor material comprising a first compound comprising a halide moiety and a metal or a metalloid, a second precursor material material comprises a second compound consisting of at least a polyatomic nonmetal and one or more amines, and a solvent to obtain a mixture solution. The method also comprises heating the mixture solution such as to colloidally form nanoparticles comprising said polyatomic nonmetal and said metal or comprising said polyatomic nonmetal and said metalloid. The different precursors are added such that an abundance of at least 2.5, preferably at least 4, of the polyatomic nonmetal relative to the metal or the metalloid is obtained in said mixture solution. The abundance of the polyatomic nonmetal relative to the metalloid may be at least 3 times, e.g. at least 4 times, e.g. at least 5 times, for example at least 10 times. The amount of polyatomic non-metal relative to the amount of the metal or the metalloid may be obtained by mixing corresponding compounds mixed in the mixture solution. Furthermore, optional steps may correspond with steps of methods as described in the first aspect. In the second precursor, the amine may comprise a dimethylamine, dipropylamine, diethylamine, dibutylamine, dioctylamine, butylamine, octylamine, dodecylamine or oleylamine. It is an advantage of such compound of one or more amines and a polyatomic non-metal that an economic synthesis can be obtained. In embodiments according to the present invention, the second precursor material may comprise a tris(dimethylamino)phosphine (DMA)$_3$P. In embodiments according to the present invention, the second precursor material may comprise a tris(diethylamino)phosphide (DEA)$_3$P. It is an advantage of (DEA)$_3$P that it is a relatively cheap product, it has advantageously a boiling point, e.g. about 240° C., that is higher than an exemplary synthesis temperature of InP, e.g. about 180° C., and furthermore has an advantageously high concentration of phosphorus, such that only a small volume of the precursor needs to be injected in the reaction mixture.

Embodiments of the present invention may relate to a method wherein a tris(amino)phosphine precursor, generally referred to as P(amino)$_3$, and an indium halide precursor, referred to as InX$_3$, are used.

In still another aspect, the present invention also relates to a colloidally formed nanoparticle comprising a polyatomic nonmetal and a metal or comprising a polyatomic nonmetal and a metalloid, the nanoparticle being formed using a method as described in the third aspect. Optional features may be as described with respect to the nanoparticles obtained using the methods of the third aspect.

The invention claimed is:

1. A method for synthesizing nanoparticles, the method comprising:

mixing a first precursor material comprising a first compound comprising a halide moiety and a metal or a metalloid, a second precursor material comprising a second compound comprising at least a polyatomic nonmetal, and a solvent to obtain a mixture solution, and heating said mixture solution such as to colloidally form nanoparticles comprising said polyatomic nonmetal and said metal or comprising said polyatomic nonmetal and said metalloid, wherein said halide moiety is selected such as to colloidally form said nanoparticles in a predetermined size range that is at least partially determined by said halide moiety and wherein an abundance of at least 2.5, of the polyatomic nonmetal relative to the metal or the metalloid is obtained in said mixture solution.

2. The method for synthesizing according to claim 1, wherein the second precursor material comprises a second compound comprising said at least a polyatomic nonmetal and an amine.

3. The method according to claim 2, wherein said amine comprises an aliphatic primary or secondary amine.

4. The method for synthesizing according to claim 1, wherein an abundance of 4 of the polyatomic nonmetal relative to the metal or the metalloid is obtained in said mixture solution.

5. The method according to claim 1, wherein said mixing comprises mixing said first precursor material comprising a plurality of different halide moieties, and
wherein the relative abundances of said plurality of different halide moieties is selected such as to colloidally form said nanoparticles in a predetermined size range at least partially determined by said relative abundances of the plurality of different halide moieties.

6. The method according to claim 1, wherein the metal or the metalloid comprises at least one of cadmium, mercury, zinc, titanium, aluminum, gallium, indium, thallium, silicon, germanium, tin, lead, arsenic, antimony, bismuth, tellurium, polonium or astatine and/or wherein the polyatomic nonmetal comprises phosphorus, sulfur or selenium.

7. The method according to claim 1, wherein said second precursor material comprises a phosphorous material.

8. The method according to claim 1, wherein said first precursor material comprises an indium halide and said second precursor material comprises tris(diethylamino) phosphine.

9. The method according to claim 1, furthermore comprising a step of degassing the mixture solution before or during said heating.

10. The method according to claim 1, in which said heating is performed under an inert atmosphere.

11. The method according to claim 1, in which said mixing comprises mixing at least one further precursor material in said mixture solution, wherein the at least one further precursor material comprises at least one further compound comprising a halide moiety and a further metal or metalloid, said further metal or metalloid being different from said metal or said metalloid in the first compound.

12. The method according to claim 11, wherein said heating comprises heating said mixture solution such as to colloidally form nanoparticles comprising said polyatomic nonmetal and said metal or metalloid of the first compound, said further metal or metalloid of the at least one further compound and said polyatomic nonmetal.

13. The method according to claim 12, wherein said first precursor material comprises an indium halide, said second precursor material comprises tris(diethylamino)phosphine and said at least one further precursor material comprises a group II metal halide.

14. The method according to claim 1, wherein mixing of the mixture solution and heating the mixture solution comprise one or both of
heating the solvent and
injecting the first precursor material and the second precursor material at a predetermined temperature of the solvent.

15. The method according to claim 1, wherein mixing of the mixture solution and heating the mixture solution comprise one or both of
heating the solvent mixed with one of the first precursor material and the second precursor material, and
injecting the other of the first precursor material and the second precursor material at a predetermined temperature.

* * * * *